US008060576B2

(12) United States Patent
Chan et al.

(10) Patent No.: US 8,060,576 B2
(45) Date of Patent: Nov. 15, 2011

(54) SYSTEM AND METHOD FOR COMMUNICATING OVER A NETWORK WITH A MEDICAL DEVICE

(75) Inventors: Johnny Yat Ming Chan, Arcadia, CA (US); Brent Chamblee, Aliso Viejo, CA (US)

(73) Assignee: Event Medical, Inc., San Clemente, CA (US)

(*) Notice: Subject to any disclaimer, the term of this patent is extended or adjusted under 35 U.S.C. 154(b) by 0 days.

(21) Appl. No.: 13/115,901

(22) Filed: May 25, 2011

(65) Prior Publication Data

US 2011/0219091 A1  Sep. 8, 2011

Related U.S. Application Data

(63) Continuation of application No. 13/004,799, filed on Jan. 11, 2011.

(60) Provisional application No. 61/296,390, filed on Jan. 19, 2010, provisional application No. 61/376,019, filed on Aug. 23, 2010.

(51) Int. Cl.
*G06F 15/16* (2006.01)

(52) U.S. Cl. ........ 709/206; 709/219; 715/205; 715/234; 381/67

(58) Field of Classification Search .................. 709/206, 709/219; 715/205, 234; 381/67
See application file for complete search history.

(56) References Cited

U.S. PATENT DOCUMENTS

| | | | |
|---|---|---|---|
| 5,692,126 A | 11/1997 | Templeton et al. | |
| 5,778,189 A | 7/1998 | Kimura et al. | |
| 5,848,415 A | 12/1998 | Guck | |
| 6,070,196 A | 5/2000 | Mullen, Jr. | |
| 6,070,798 A | 6/2000 | Nethery | |
| 6,246,677 B1 | 6/2001 | Nap et al. | |
| 6,260,021 B1 | 7/2001 | Wong et al. | |
| 6,272,468 B1 | 8/2001 | Melrose | |
| 6,304,788 B1 | 10/2001 | Eady et al. | |
| 6,389,464 B1 | 5/2002 | Krishnamurthy et al. | |
| 6,473,638 B2 | 10/2002 | Ferek-Petric | |
| 6,526,970 B2 | 3/2003 | DeVries et al. | |
| 6,539,940 B2 | 4/2003 | Zdrojkowski et al. | |
| 6,574,629 B1 | 6/2003 | Cooke et al. | |
| 6,626,175 B2 | 9/2003 | Jafari et al. | |
| 6,635,016 B2 | 10/2003 | Finkelshteins | |
| 6,644,311 B1 | 11/2003 | Truitt et al. | |
| 6,672,300 B1 | 1/2004 | Grant | |
| 6,734,880 B2 | 5/2004 | Chang et al. | |
| 6,761,165 B2 | 7/2004 | Strickland et al. | |
| 6,781,522 B2 | 8/2004 | Sleva et al. | |
| 6,782,888 B1 | 8/2004 | Friberg et al. | |
| 6,839,753 B2 | 1/2005 | Biondi et al. | |
| 6,848,444 B2 | 2/2005 | Smith et al. | |
| 6,871,211 B2 | 3/2005 | Labounty et al. | |
| 6,877,511 B2 | 4/2005 | DeVries et al. | |
| 6,911,916 B1 | 6/2005 | Wang et al. | |
| 6,918,125 B1 | 7/2005 | Skinner et al. | |
| 6,932,084 B2 | 8/2005 | Estes et al. | |

(Continued)

FOREIGN PATENT DOCUMENTS

EP   1 286 280 A1   2/2003

(Continued)

*Primary Examiner* — Kyung H Shin

(74) *Attorney, Agent, or Firm* — Knobbe, Martens, Olson & Bear LLP

(57) ABSTRACT

A device is provided for connecting a medical apparatus to a network. The device collects data from the medical apparatus and performs a variety of processing functions, such as trending, protocol translation, generating reports, etc. related to the collected data. The device then transmits the collected data over a network to interested parties. In some implementations, the device can transmit the collected data as an email message.

11 Claims, 11 Drawing Sheets

U.S. PATENT DOCUMENTS

| | | |
|---|---|---|
| 6,943,787 B2 | 9/2005 | Webb |
| 6,947,581 B1 | 9/2005 | Patel et al. |
| 6,955,171 B1 | 10/2005 | Figley et al. |
| 6,956,572 B2 | 10/2005 | Zaleski |
| 6,962,154 B2 | 11/2005 | Krebs |
| 6,963,673 B1 | 11/2005 | Patel et al. |
| 7,007,692 B2 | 3/2006 | Aylsworth et al. |
| 7,020,868 B2 | 3/2006 | Debbins et al. |
| 7,040,318 B2 | 5/2006 | Dascher et al. |
| 7,063,086 B2 | 6/2006 | Shahbazpour et al. |
| 7,077,131 B2 | 7/2006 | Hansen |
| 7,082,334 B2 | 7/2006 | Boute et al. |
| 7,127,299 B2 | 10/2006 | Nelson et al. |
| 7,127,300 B2 | 10/2006 | Mazar et al. |
| 7,134,434 B2 | 11/2006 | Truitt et al. |
| 7,152,604 B2 | 12/2006 | Hickle et al. |
| 7,188,621 B2 | 3/2007 | DeVries et al. |
| 7,201,166 B2 | 4/2007 | Blaise et al. |
| 7,207,331 B2 | 4/2007 | Mashak |
| 7,219,666 B2 | 5/2007 | Friberg et al. |
| 7,255,105 B2 | 8/2007 | Figley et al. |
| 7,264,590 B2 | 9/2007 | Casey et al. |
| 7,275,540 B2 | 10/2007 | Bolam et al. |
| 7,305,988 B2 | 12/2007 | Acker et al. |
| 7,319,386 B2 | 1/2008 | Collins, Jr. et al. |
| 7,320,321 B2 | 1/2008 | Pranger et al. |
| 7,327,705 B2 | 2/2008 | Fletcher et al. |
| 7,331,343 B2 | 2/2008 | Schmidt et al. |
| 7,334,578 B2 | 2/2008 | Biondi et al. |
| 7,349,947 B1 | 3/2008 | Slage et al. |
| 7,382,247 B2 | 6/2008 | Welch et al. |
| 7,400,257 B2 | 7/2008 | Rivas |
| 7,408,439 B2 | 8/2008 | Wang et al. |
| 7,430,608 B2 | 9/2008 | Noonan et al. |
| 7,448,381 B2 | 11/2008 | Sasaki et al. |
| 7,448,382 B1 | 11/2008 | Alexander et al. |
| 7,468,032 B2 | 12/2008 | Stahmann et al. |
| 7,515,043 B2 | 4/2009 | Welch et al. |
| 7,515,044 B2 | 4/2009 | Welch et al. |
| 7,706,820 B2 | 4/2010 | Yamaki |
| 7,734,756 B2 | 6/2010 | Linderman |
| 7,840,694 B2 | 11/2010 | Yamaki |
| 7,844,657 B2 | 11/2010 | Novak |
| 7,849,140 B2 | 12/2010 | Abdel-Aziz et al. |
| 2002/0035638 A1 | 3/2002 | Gendron et al. |
| 2002/0116637 A1 | 8/2002 | Deitsch et al. |
| 2002/0133061 A1 | 9/2002 | Manetta |
| 2003/0107487 A1 | 6/2003 | Korman et al. |
| 2004/0078226 A1 | 4/2004 | Becker et al. |
| 2004/0210664 A1 | 10/2004 | Prendergast |
| 2005/0080322 A1 | 4/2005 | Korman et al. |
| 2005/0177312 A1 | 8/2005 | Guerrant et al. |
| 2005/0257257 A1 | 11/2005 | O'Connor et al. |
| 2006/0013458 A1 | 1/2006 | Debbins et al. |
| 2006/0047538 A1 | 3/2006 | Condurso et al. |
| 2006/0052842 A1 | 3/2006 | Hess et al. |
| 2006/0154642 A1 | 7/2006 | Scannell |
| 2006/0173719 A1 | 8/2006 | Kuhn et al. |
| 2006/0235280 A1 | 10/2006 | Vonk et al. |
| 2006/0242159 A1 | 10/2006 | Bishop et al. |
| 2007/0015973 A1 | 1/2007 | Nanikashvili |
| 2007/0044799 A1 | 3/2007 | Hete et al. |
| 2007/0062530 A1 | 3/2007 | Weismann et al. |
| 2007/0088521 A1 | 4/2007 | Shmueli et al. |
| 2007/0125377 A1 | 6/2007 | Heinonen et al. |
| 2007/0125381 A1 | 6/2007 | Mashak |
| 2007/0135866 A1 | 6/2007 | Baker et al. |
| 2007/0144516 A1 | 6/2007 | Doyle |
| 2007/0163579 A1 | 7/2007 | Li et al. |
| 2007/0185547 A1 | 8/2007 | Hoyme et al. |
| 2007/0185739 A1 | 8/2007 | Ober et al. |
| 2007/0186928 A1 | 8/2007 | Be'Eri |
| 2007/0191912 A1 | 8/2007 | Fischer et al. |
| 2007/0193579 A1 | 8/2007 | Duquette et al. |
| 2007/0197881 A1 | 8/2007 | Wolf et al. |
| 2007/0215154 A1 | 9/2007 | Borrello |
| 2007/0227540 A1 | 10/2007 | Ljungberg et al. |
| 2007/0240718 A1 | 10/2007 | Daly |
| 2007/0253380 A1 | 11/2007 | Jollota et al. |
| 2007/0254593 A1 | 11/2007 | Jollota et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0299480 A1 | 12/2007 | Hill |
| 2008/0004904 A1 | 1/2008 | Tran |
| 2008/0005054 A1 | 1/2008 | Kurian et al. |
| 2008/0011302 A1 | 1/2008 | Bassin |
| 2008/0019393 A1 | 1/2008 | Yamaki |
| 2008/0051667 A1 | 2/2008 | Goldreich |
| 2008/0058884 A1 | 3/2008 | Matos |
| 2008/0059228 A1 | 3/2008 | Bossie et al. |
| 2008/0071328 A1 | 3/2008 | Haubrich et al. |
| 2008/0072904 A1 | 3/2008 | Becker et al. |
| 2008/0078386 A1 | 4/2008 | Feldhahn et al. |
| 2008/0091175 A1 | 4/2008 | Frikart et al. |
| 2008/0092891 A1 | 4/2008 | Cewers |
| 2008/0094207 A1 | 4/2008 | Collins, Jr. et al. |
| 2008/0097552 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097914 A1 | 4/2008 | Dicks et al. |
| 2008/0110458 A1 | 5/2008 | Srinivasan et al. |
| 2008/0120284 A1 | 5/2008 | Profio et al. |
| 2008/0121232 A1 | 5/2008 | Cewers |
| 2008/0121233 A1 | 5/2008 | von Blumenthal et al. |
| 2008/0127975 A1 | 6/2008 | Lirsch et al. |
| 2008/0140163 A1 | 6/2008 | Keacher et al. |
| 2008/0141107 A1 | 6/2008 | Catallo et al. |
| 2008/0142013 A1 | 6/2008 | Hallett et al. |
| 2008/0142019 A1 | 6/2008 | Lewis et al. |
| 2008/0143538 A1 | 6/2008 | Young et al. |
| 2008/0154099 A1 | 6/2008 | Aspel et al. |
| 2008/0167902 A1 | 7/2008 | Baba et al. |
| 2008/0168990 A1 | 7/2008 | Cooke et al. |
| 2008/0173304 A1 | 7/2008 | Zaiser et al. |
| 2008/0190429 A1 | 8/2008 | Tatarek |
| 2008/0190431 A1 | 8/2008 | Bellefeuille |
| 2008/0196720 A1 | 8/2008 | Kollmeyer et al. |
| 2008/0210237 A1 | 9/2008 | McAuliffe et al. |
| 2008/0215360 A1 | 9/2008 | Dicks et al. |
| 2008/0216834 A1 | 9/2008 | Easley et al. |
| 2008/0221918 A1 | 9/2008 | Petersen et al. |
| 2008/0230059 A1 | 9/2008 | Mashak et al. |
| 2008/0245366 A1 | 10/2008 | Lee |
| 2008/0251077 A1 | 10/2008 | Durtschi et al. |
| 2008/0255885 A1 | 10/2008 | Eisenberger et al. |
| 2008/0264417 A1 | 10/2008 | Manigel et al. |
| 2008/0288294 A1 | 11/2008 | Eisenberger et al. |
| 2009/0072962 A1 | 3/2009 | Hitchin |
| 2009/0073991 A1 | 3/2009 | Landrum et al. |
| 2009/0112630 A1 | 4/2009 | Collins, Jr. et al. |
| 2009/0193435 A1 | 7/2009 | Yamaki |
| 2009/0234672 A1 | 9/2009 | Dicks et al. |
| 2010/0235518 A1 | 9/2010 | Holden et al. |
| 2011/0001605 A1 | 1/2011 | Kiani et al. |
| 2011/0087756 A1 | 4/2011 | Biondi et al. |

FOREIGN PATENT DOCUMENTS

| | | |
|---|---|---|
| EP | 1 414 509 B1 | 11/2008 |
| WO | WO 98/24358 | 6/1998 |
| WO | WO 98/37704 A2 | 8/1998 |
| WO | WO 00/59566 A1 | 10/2000 |
| WO | WO 01/32069 A2 | 5/2001 |
| WO | WO 02/28123 A2 | 4/2002 |
| WO | WO 03/013635 A1 | 2/2003 |
| WO | WO 2005/050519 A1 | 6/2005 |
| WO | WO 2005/071895 A1 | 8/2005 |
| WO | WO 2005/076535 A1 | 8/2005 |
| WO | WO 2005/110238 A1 | 11/2005 |
| WO | WO 2005/117389 A1 | 12/2005 |
| WO | WO 2006/108304 A1 | 10/2006 |
| WO | WO 2010/068356 A2 | 6/2010 |

SYSTEM AND METHOD FOR COMMUNICATING OVER A NETWORK WITH A MEDICAL DEVICE

CROSS REFERENCE TO RELATED APPLICATIONS

This application is a continuation of U.S. patent application Ser. No. 13/004,799, filed Jan. 11, 2011, which claims the benefit of U.S. provisional application No. 61/296,390, filed Jan. 19, 2010, and U.S. provisional application No. 61/376,019, filed Aug. 23, 2010, the disclosures of which are hereby incorporated by reference in their entirety.

BACKGROUND

1. Field

The present disclosure relates to computer systems for communicating over a network with a medical device.

2. Description of the Related Art

The sharing of patient data between medical institutions and health care providers presents a variety of challenges. These challenges may include privacy, expense, accessibility, etc.

In 1996, President Clinton signed the Health Insurance Portability and Accountability Act (HIPAA). Among other things, this law (i) ensures the continuity of healthcare coverage for individuals changing jobs; (ii) includes a provision that impacts the management of health information; (iii) seeks to simplify the administration of health insurance; and (iv) aims to combat waste, fraud and abuse in health insurance and healthcare.

The Department of Health and Human Services has issued various regulations to implement these new requirements. These regulations impact all healthcare organizations that electronically create, store and/or transmit healthcare data. Among other things, HIPAA requires the secure storage and transmission of electronic healthcare data.

Setting up Virtual Private Networks (VPNs) or running point-to-point T1 lines can provide the necessary secure transmission of electronic healthcare data. However, VPNs and T1 lines can be cost prohibitive in many situations.

Alternatively, the so-called secure shell (SSH) technology and rsync protocol can be used to provide a suite of network connectivity tools which enable secure transmission of electronic healthcare data by creating a minimal subset of a many-to-one virtual network running over the public Internet.

In addition to the foregoing, medical institutions (e.g., hospitals) typically implement firewalls to limit outside access to their internal computer networks. Among other things, hospital firewalls will typically block outside attempts to access any medical data on their internal medical devices. One example of such a device is described in U.S. Pat. No. 7,040,318, the disclosure of which is hereby incorporated by reference. Outside access to such devices, even if they included an embedded server as described, is typically blocked by medical institutions.

Unfortunately, in many situations, it can be important for a healthcare provider to have access to the medical data on internal medical devices outside the healthcare institution. For example, it may be desirable to pass collected medical data from the hospital to a physician for analysis. In circumstances such as these, the aforementioned security systems for storing and transmitting electronic healthcare data can impede the electronic transfer of the data.

BRIEF DESCRIPTION OF THE DRAWINGS

Aspects and many of the attendant advantages of this disclosure will become more readily appreciated as the same become better understood by reference to the following detailed description, when taken in conjunction with the accompanying drawings, wherein.

DETAILED DESCRIPTION OF THE PREFERRED EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Systems, methods, and computer-readable media are disclosed for communicating over a network with, and obtaining medical data from, a medical device. More specifically, systems, methods, and computer readable media are disclosed for enabling an entity external to a medical institution that has a firewall or other network security system to communicate with a medical device in the medical institution.

For example, in one embodiment, a medical device is provided that performs a requested action. The medical device then generates a response that is dependent upon the requested action and sends the generated response to a node on a network from the medical device as an email message.

In another embodiment, a method of communicating with a medical device over a network is provided. The method comprises receiving over the network, by the medical device, a request to perform some action from a node, such as, an email server. The medical device then performs the requested action, wherein the request is received as an email. FIGS. 1-7 illustrate various exemplary embodiments of the invention in more detail.

Figure 1:
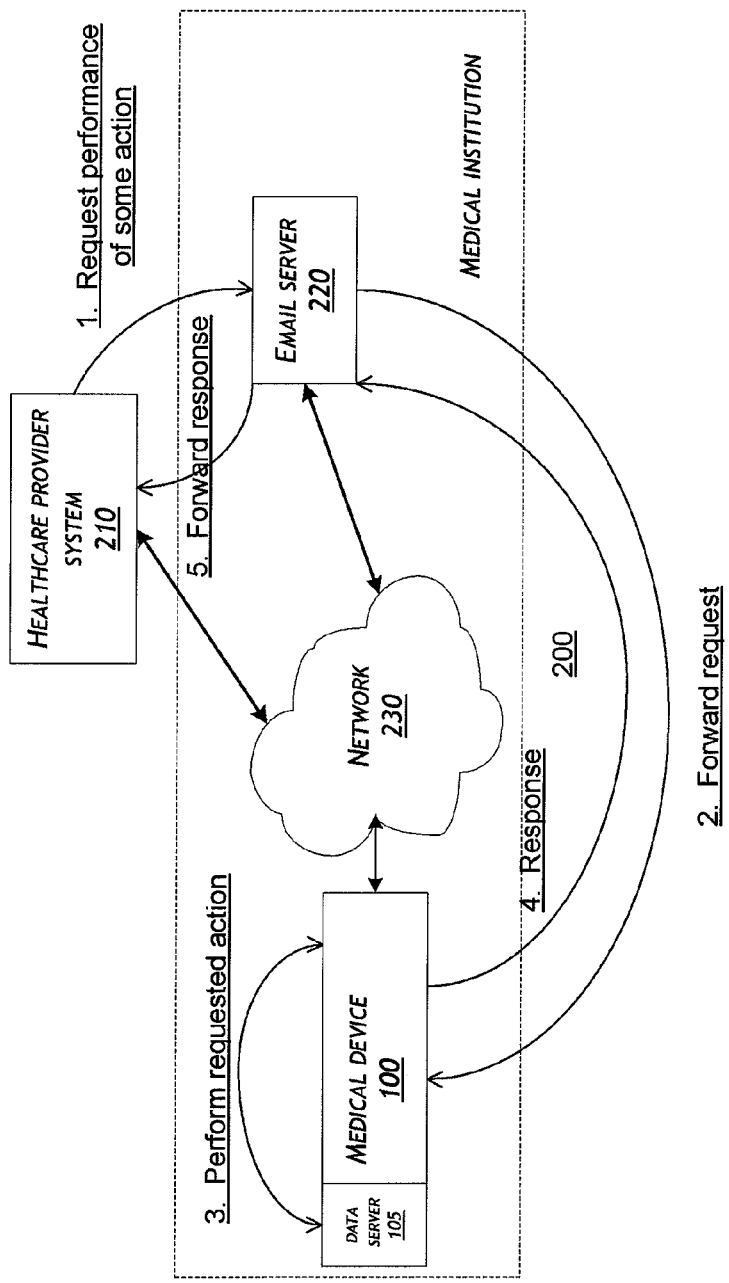
FIG. 1 is a block diagram of the system according to one embodiment.

FIG. 1 illustrates an exemplary system environment 200 for implementing embodiments of the invention. As shown in FIG. 1, system 200 may comprise multiple computer systems or machines, such as, a healthcare provider system 210 (which may be implemented as a "client"), a medical device 100 containing a data server 105, and an email server 220. These various components may be connected and communicate with one another through any suitable network 230, including the Internet. Email server 220 may be a conventional, preexisting system operated by its respective entity.

Healthcare provider system 210 may comprise any computing system used to perform tasks of some embodiments of the invention. In one embodiment, healthcare provider system 210 is maintained by a healthcare provider that desires access to medical device 100. Healthcare provider system 210 is provided a web interface such that a healthcare provider may interact with email server 220. Healthcare provider system 210 may be located at any location, such as a healthcare provider's home, office, or kiosk, etc. Additionally, one skilled in the art will appreciate that any number of healthcare provider systems may be provided to enable access to medical device 100 by healthcare providers.

Email server 220 is maintained by an entity that provides email service to employees or people associated with a medical institution. For example, email server 220 may be maintained by Google, Yahoo, etc. In a preferred embodiment, email server 220 is maintained by a hospital.

Medical device 100 is maintained by a medical institution. Medical device 100 is used by a medical institution to collect data from patients and to treat patients. Medical device 100 includes a data server 105. In a preferred embodiment, medical device 100 is a ventilator including a data server 105, such as the ventilator described in U.S. Pat. No. 7,040,318 and incorporated herein by reference. In an alternate embodiment, medical device 100 may be an implanted medical device, such a defibrillator, pacemaker, etc., that communicates with data server 105. That is, the implanted medical device may communicate with data server 105 via a wireless link, such as an RF link. A skilled artisan will appreciate that a variety of other configurations and communication mechanisms are possible in embodiments of the present invention. Further, in a preferred embodiment, medical device 100 is associated with a unique email address.

As shown in FIG. 1, in a preferred embodiment, medical device 100 is located within a medical institution and healthcare provider 210 is located outside of the medical institution. Some embodiments of the present invention enable communication between healthcare provider 210 and medical device 100 even if the medical institution has established security measures (e.g., firewalls), as discussed above. In some embodiments of the present invention, email server 220 may be located either inside or outside the medical institution. A skilled artisan would appreciate that healthcare provider system 210 located within the medical institution would also be configured to communicate with medical device 100 in some embodiments of the present invention. A skilled artisan would also appreciate that in some embodiments of the present invention, healthcare provider system 210 would be configured to communicate with medical device 100 even if the medical institution had not established the security measures discussed above.

FIG. 1 also shows an exemplary sequence of steps (1-5) that may be performed by system environment 200 in one embodiment. The communications shown in FIG. 1 occur over one or more computer networks, such as the Internet and/or an internal network of the medical institution. First (1), healthcare provider system 210 requests the performance of some action associated with the medical device (e.g., a request for a particular item or type of data), and the request is sent to email server 220. This request may be in the form of an email. This request may be generated automatically by a special application, e.g., on input from a human operator. The type of action to be performed may be specified explicitly or implicitly in the request message. Next (2), email server 220 forwards the request to medical device 100. Then (3), medical device 100 performs the requested action and (4) sends a response to email server 220. This response may be in the form of an email reply, and may include physiologic and/or other data collected by the medical device 100 from one or more patients. Finally (5), email server 220 forwards the response to healthcare provider system 210. More detail regarding the sequence of steps will be discussed below in relation to FIGS. 4 and 5. Because the communications (1) and (5) between the medical institution and the healthcare provider system 210 can be email communications, they are not susceptible to being blocked by the medical institution's Internet firewall.

Although a single medical device is depicted in FIG. 1, many different medical devices 100 that operate as described above may be provided within the medical institution, and each may have a unique email address. In addition, multiple distinct healthcare provider entities and systems 210 may communicate with a particular medical device using the method shown in FIG. 1.

In some cases, multiple email addresses may be assigned to a given medical device 100, and the type of operation performed by the medical device 100 in response to the request may depend on the address used. For instance, an email sent to device123-data1@hospital.com may cause the device 100 to return one type of medical data, while an email sent to device123-data2@hospital.com may cause the device 100 to return another type of data.

Figure 2:
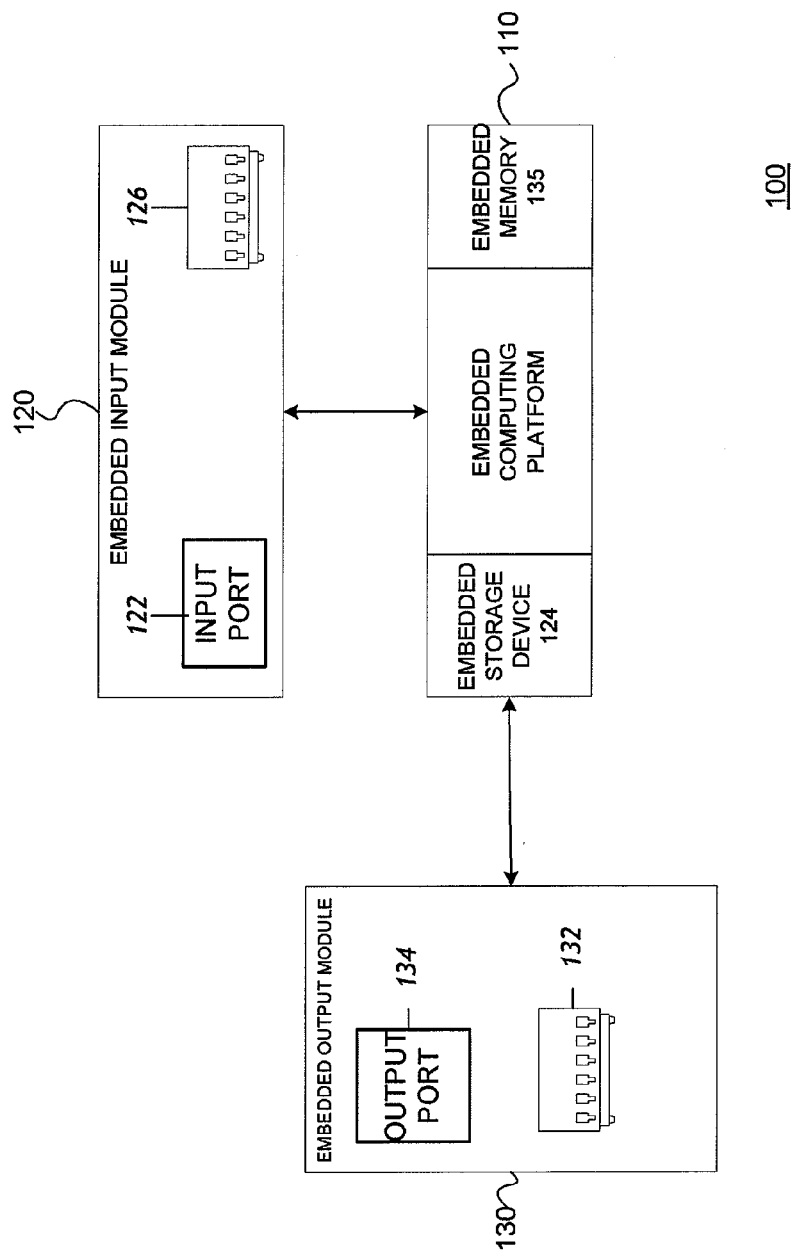
FIG. 2 illustrates the components of the medical device of FIG. 1, in accordance with one embodiment of the invention

FIG. 2 illustrates a more detailed diagram of an exemplary medical device 100 of some embodiments of the present invention. In this example, medical device 100 facilitates the communication of medical data and in particular communication of medical data outside of medical institutions in the preferred embodiment.

As illustrated in FIG. 2, medical device 100 includes an embedded computing platform 110, an embedded input module 120, an embedded output module 130, and an embedded memory 135. Embedded computing platform 110 may be adapted to process input information received from embedded input module 120. Embedded computing platform 110 may further be adapted to provide output information to embedded output module 130.

Embedded computing platform 110 may comprise a general purpose computer (e.g., a personal computer, network computer, server, or mainframe computer) having a processor that may be selectively activated or reconfigured by a computer program to perform one or more methods of the present invention. Embedded computing platform 110 may also be implemented in a distributed network. Alternatively, embedded computing platform 110 may be specially constructed for carrying-out methods of the present invention, such as through the use of application-specific circuitry.

Embedded input module 120 may include an input port 122 and/or an embedded network interface 126. Input port 122 may comprise one or more ports that may be connected to patients, other medical devices, other computing devices, etc. to collect medical data that is to be communicated. Embedded network interface 126 may receive information over any type of network (not shown), such as a telephony-based network (e.g., PBX or POTS), a local area network, a wide area network, a dedicated intranet, and/or the Internet. Embedded computing platform 110 may also access data stored on embedded storage device 124. Embedded storage device 124 may include a memory, such as RAM or ROM memory, that contains instructions or data for performing one or more methods of the present invention.

Embedded output module 130 may include an output port 132 and an embedded output interface 134. Output port 132 may be connected to patients, other medical devices, other computing devices, etc. to transmit medical data, commands, requests, etc. that are received. Output port 132 may also be used to control patients, other medical devices, other computing devices, etc. Embedded output interface 134 may be used to provide relevant information to the interested parties via the Internet, email, fax, page, etc. or save the information on a computer readable medium.

Figure 2A:
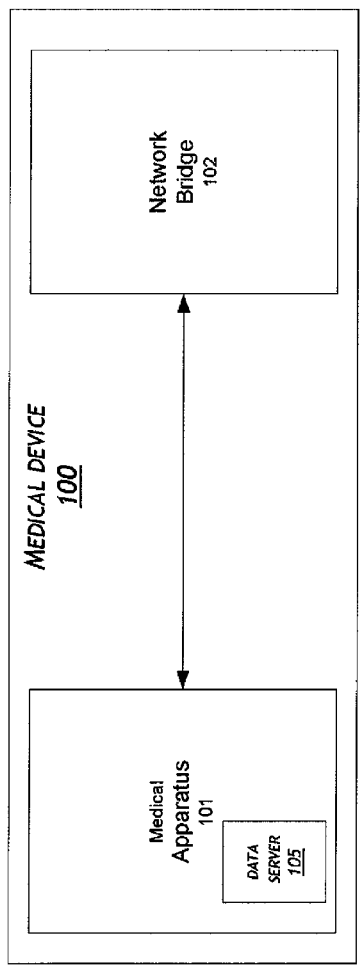
FIG. 2A illustrates one system configuration for the medical device of FIG. 2, in accordance with one embodiment of the invention.

FIG. 2A shows one example of a system configuration that can be used to implement medical device 100. In this embodiment, medical device 100 may comprise medical apparatus 101 and network bridge 102. Medical apparatus, as described above, is used by a medical institution to collect data from patients and to treat patients. Medical apparatus 101 includes data server 105. As also discussed above, in a preferred embodiment, medical apparatus 101 is a ventilator including a data server 105, such as the ventilator described in U.S. Pat. No. 7,040,318 and incorporated herein by reference. In an alternate embodiment, medical apparatus 100 may be an implanted or implantable medical device, such a defibrillator, pacemaker, etc., that communicates with data server 105. Medical apparatus 101 can be configured to provide one or more ports to communicate with patients or external devices. For instance, medical apparatus 100 may include one or more ports configured to provide the functionality of input port 122 and/or output port 132. Data server 105 is configured to include embedded computing platform 110, embedded memory 135, and embedded storage device 124, as described above (not shown). Data server 105 is configured to manage the medical data and provide the functionality discussed below. For example, data server 105 may store and analyze collected medical data. For instance, data server 105 may generate reports, charts, trending or other quantitative analysis, web pages for the medical data or applets for viewing the medical data.

Medical apparatus 101 also has one or more ports configured to connect to network bridge 102. Network bridge 102 is configured to provide the functionality of network interface 126 and/or output interface 134. For instance, network bridge 102 may be a wireless transceiver or modem that connects medical apparatus 101 to network 230. As another example, network bridge 102 may be an Ethernet card or integrated circuit. Network bridge 102 transmits data from medical apparatus 101 to network 230 and receives data from network 230 and sends data back to medical apparatus 101. In order for network bridge 102 to receive and send data, network bridge 102 can be configured to translate the data to various formats. For example, network bridge 102 can be configured to translate serial data from medical apparatus 101 to TCP/IP or UDP packets for transmission over network 230. A skilled artisan will appreciate that network bridge 102 may perform a variety of protocol translations known in the art.

Figure 2B:
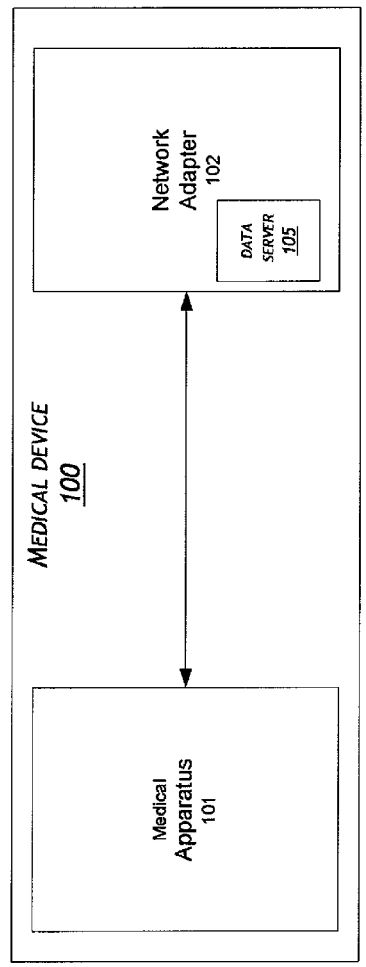
FIG. 2B illustrates an alternative system configuration for the medical device of FIG. 2, in accordance with one embodiment of the invention.

FIG. 2B shows another example of a system configuration that can be used to implement medical device 100. In this embodiment, medical device 100 may also comprise medical apparatus 101 and network bridge 102, as described above in reference to FIG. 2A. Medical apparatus 101, as also discussed above in reference to FIG. 2A, can be used by a medical institution to collect data from patients and to treat patients. As also discussed with reference to FIG. 2A, medical apparatus 101 can also be configured to provide one or more ports to communicate with patients or external devices, such as input port 122 and/or output port 132.

In contrast to FIG. 2A, data server 105 comprising embedded computing platform 110, embedded memory 135, and embedded storage device 124 may be included in network bridge 102 instead of medical apparatus 101. Data server 105, as discussed above, is configured to manage the medical data and provide the functionality discussed below. One advantage of this alternative configuration, in this embodiment, is that the processing by the data server 105 is provided by network bridge 102 instead of medical apparatus 101. As a consequence, medical apparatus 101 does not have to be programmed or configured to provide processing of data server 105. That is, network bridge 102 can be connected to any medical apparatus 101 and the processing of data server 105 can be provided without programming or configuring medical apparatus 101. In addition, since storage of medical data is handled by data server 105, including data server 105 in network apparatus 102 may require less storage space requirements by medical apparatus 101.

Another advantage of the alternative embodiment is that medical apparatus 101 of FIG. 2A is configured to output data in a specified format so that the medical data can properly be processed by network bridge 102. For example, if network bridge 102 is a wireless transceiver, medical apparatus 101 must be configured to output medical data in the proper wireless protocol standard so that it can be processed by the wireless transceiver. As such, if a different network bridge 102 is used, medical apparatus 101 would have to be re-configured to output medical data in a different format. This can be done by replacing medical apparatus 101 with a different medical apparatus or manually updating the functioning of medical apparatus 101 by uploading a different version of the software that enables outputting the medical data in a different format. This can be troublesome if multiple medical apparatuses have been installed because multiple medical apparatuses may have to be replaced or updated manually.

However, these challenges can be overcome in the embodiment of FIG. 2B. In this embodiment, medical apparatus 101 can be configured to output medical data in a standard format to network bridge 102. Then data server 105 of network bridge 102 can be adapted to format the received medical data in a specified format for transfer to network 230. This embodiment enables the communication of medical data over a variety of networks using a variety of different protocols without re-configuring or programming medical apparatus 101. Medical apparatus 101 can still communicate medical data in a standard format, such as using a RS232 port, and network bridge 102 can be reconfigured to format the medical data in a different format as may be needed.

To enable proper reformatting of the received medical data, network bridge 102 can be adapted to map the received medical data in a standard format to medical data in a specified format for transmission to network 230. That is, network bridge 102 may have a mapping table that associates medical data in the standard format to the related variables, fields for the formats for transmission to network 230. A skilled artisan will also appreciate that the standard format can be any format desired.

Figure 2C:
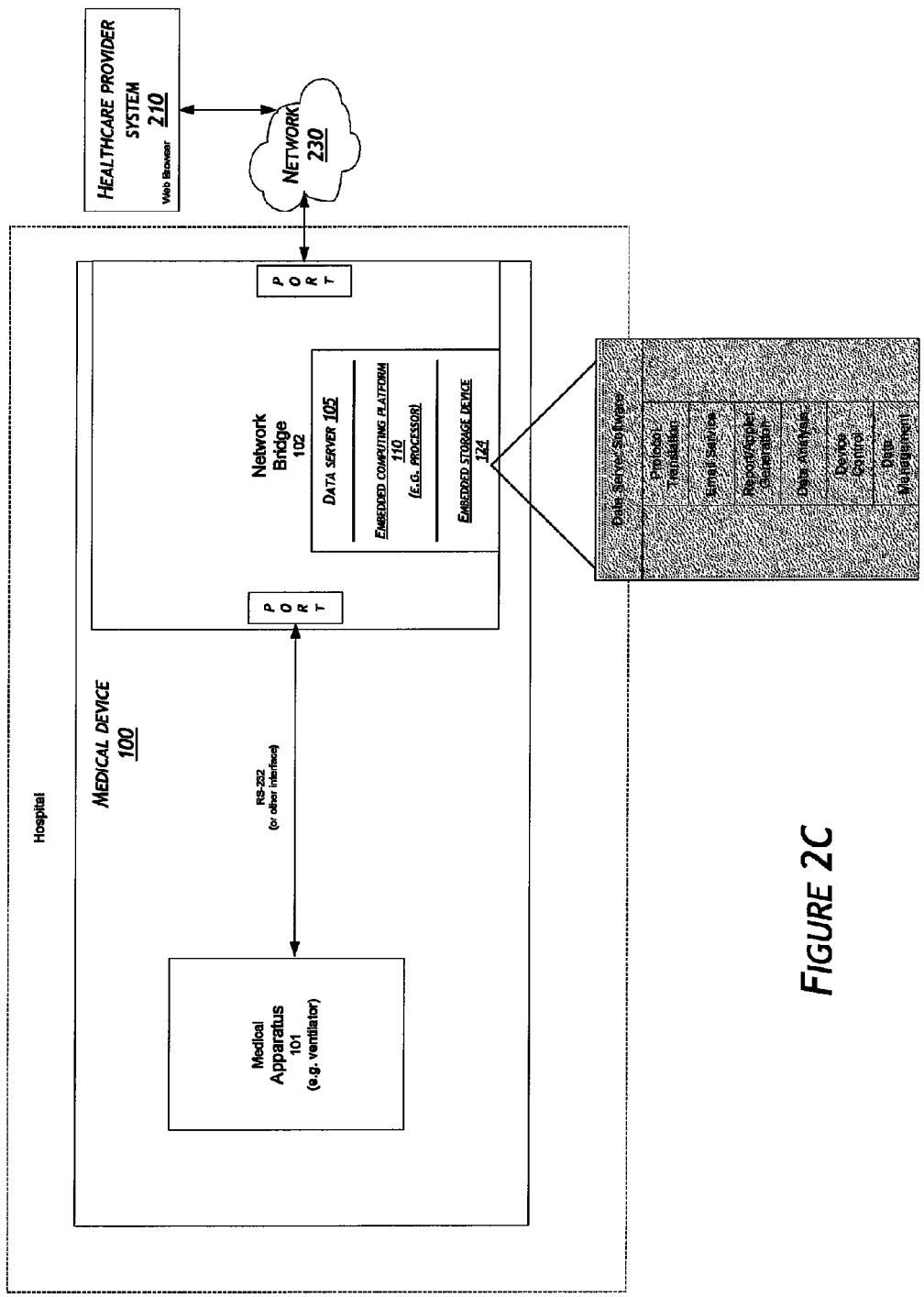
FIG. 2C illustrates another system configuration for the medical device of FIG. 2, in accordance with one embodiment of the invention.

FIG. 2C shows a more detailed embodiment of medical device 100. As described above in reference to FIG. 2B, medical device 100 can be located in a hospital and comprise medical apparatus 101 and network bridge 102. Medical apparatus 101 can be configured to output medical data in a standard format to network bridge 102. Medical apparatus 101 can be a ventilator and can be connected to network bridge 102 via an RS232 port, as shown in FIG. 2C. Data server 105, as discussed above with reference to FIG. 2, can comprise embedded computing platform 110 (e.g., a processor) and embedded storage device 124. Embedded storage device 124 may contain instructions and/or data for performing one or more methods of the present invention by embedded computing platform 110. For example, as shown, embedded storage device 124 may include executable program instructions for performing protocol translation, for providing an email, notification/alarm, web, database/SQL, etc. service, for managing the control of medical apparatus 101, for generating reports or applets, for performing data analysis, for performing data storage and management, etc. Data analysis can constitute any kind of analysis that could be performed by data server 105. For instance, data server 105 could perform trending or other statistical analysis on the medical data, could perform data mining or merging on the medical data, could perform data modeling of the medical data, etc. A skilled artisan would appreciate that data server 105 may also provide a medical recommendation or diagnosis service based on the data analysis. For example, data server 105 may determine a diagnosis or recommendation for treatment to provide to a user after analyzing the data for trends or patterns. Similarly, data server 105 can perform analysis of the medical data in comparison to previously received or stored medical data and detect any patterns, any alarms conditions, any trends, any diagnosis, etc. and notify any responsible user. A skilled artisan would also appreciate that a variety of other functions could be performed by data server 105. Network bridge 102 can be connected to network 203 via a port. Network 230 is connected to a client device, such as healthcare provider system 210 that in a preferred embodiment includes a web browser.

For instance, first, healthcare provider system 210 may request the performance of some action associated with the medical device (e.g., a request for a particular item or type of data), and the request is sent network bridge 102. This request may be in the form of an email. This request may be generated automatically by a special application, e.g., on input from a human operator. The type of action to be performed may be specified explicitly or implicitly in the request message. Next, network bridge 102 may translate the received request into a standard format for transmission to medical apparatus 101. For example, network bridge 102 may translate the email request into the standard format for transmission via the RS232 port. Then, medical apparatus 101 performs the requested action and sends a response to network bridge 102 in the standard format. Network bridge 102 then can translate the received response into a specified format for transmission to healthcare provider system 210. This response may be in the form of an email reply, and may include physiologic and/or other data collected by medical apparatus 101 from one or more patients. Network bridge 102 may also perform the various functions discussed above, such as generating reports, generating applets, performing data analysis, performing data storage and management, etc More detail regarding the sequence of steps will be discussed below in relation to FIGS. 4 and 5.

Figure 2D:
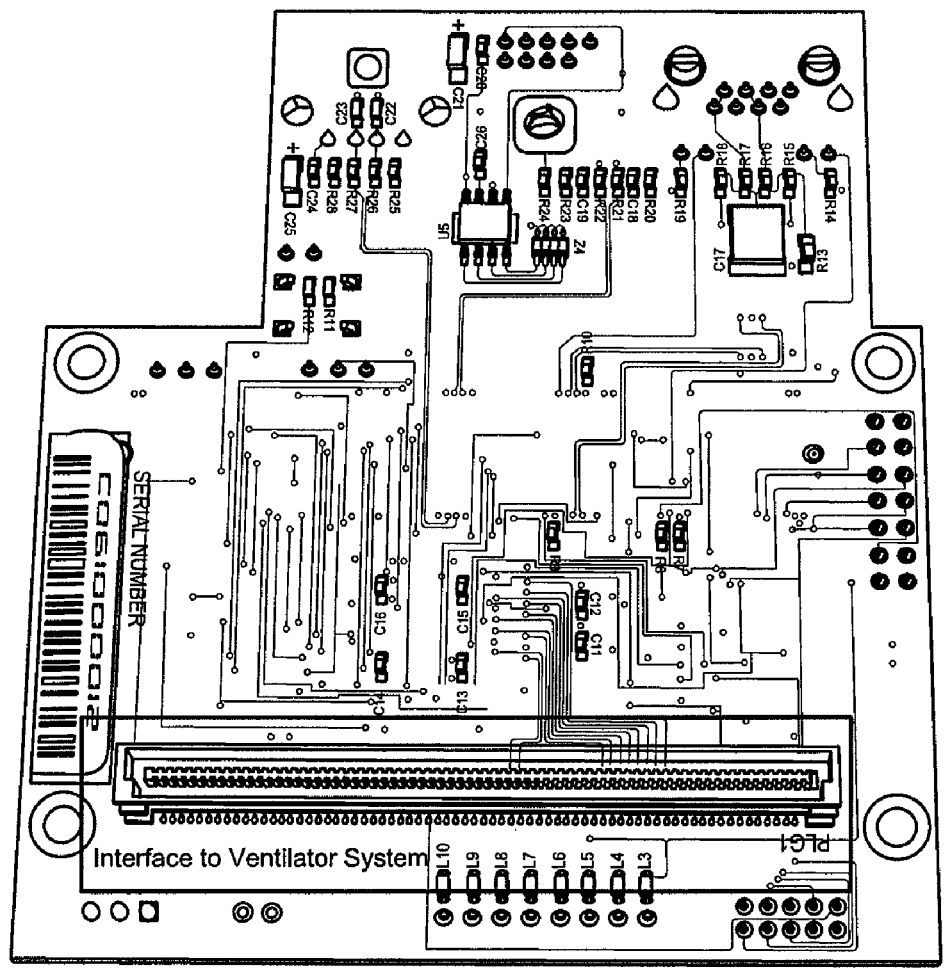
FIG. 2D illustrates a back view of an exemplary hardware configuration for the medical device of FIG. 2, in accordance with one embodiment of the invention.
Figure 2E:
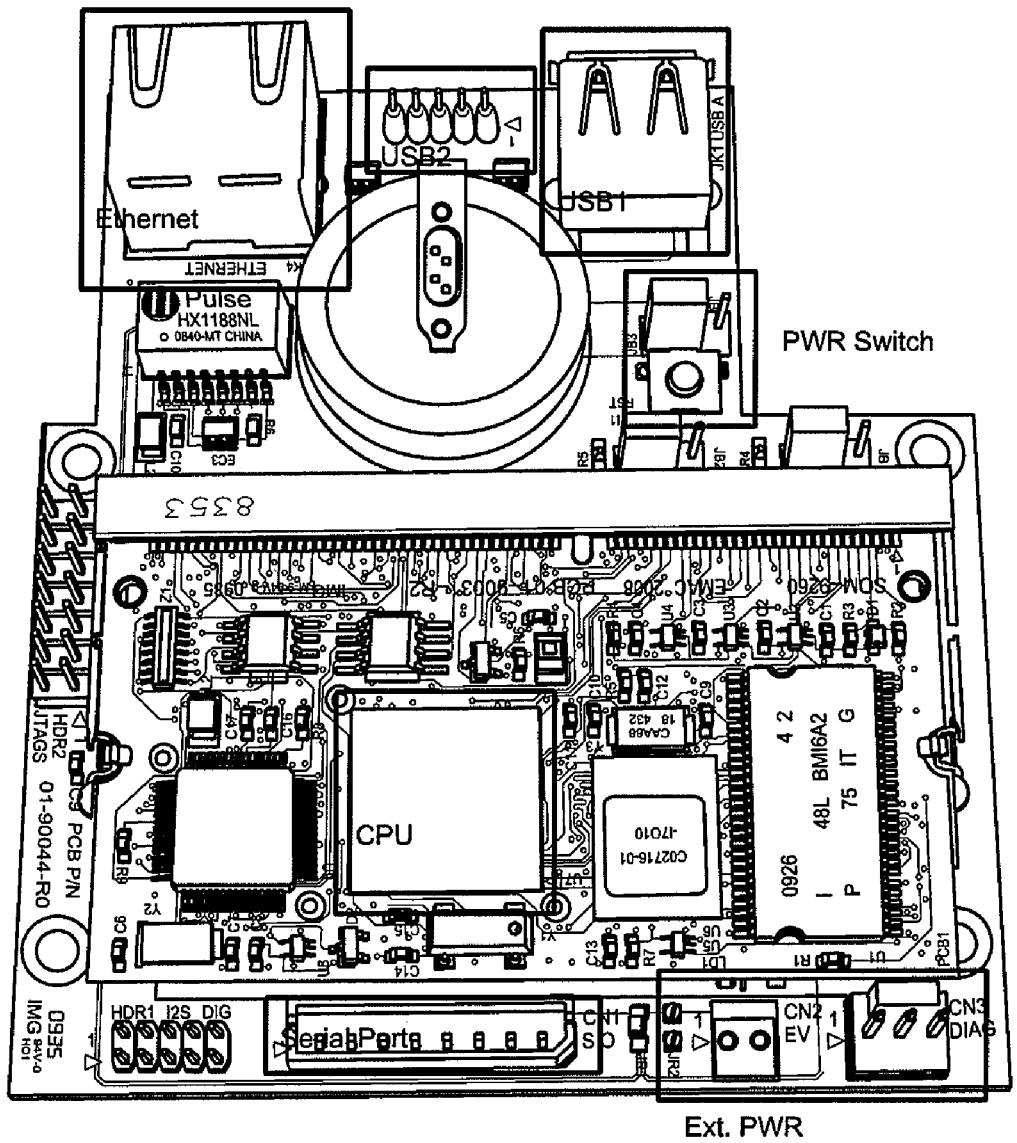
FIG. 2E illustrates a front view of an exemplary hardware configuration for the medical device of FIG. 2, in accordance with one embodiment of the invention.

FIGS. 2D and 2E illustrate an exemplary hardware configuration (circuit board) that may be used for network bridge 102. FIG. 2D illustrates the back side of the circuit board, and FIG. 2E illustrates the front side. As shown in FIG. 2D, the board may comprise an interface port to connect to medical apparatus 101, such as a ventilator. As shown in FIG. 2E, the board may also comprise a CPU, USB ports, a serial port, an Ethernet port, a power switch, and an external power port. A skilled artisan will appreciate that the serial port, USB ports, and/or Ethernet port may be used to connect to other devices or networks, as discussed above. A skilled artisan will also appreciate that a variety of other hardware or board configurations may be used in embodiments of the present invention.

Figure 3:
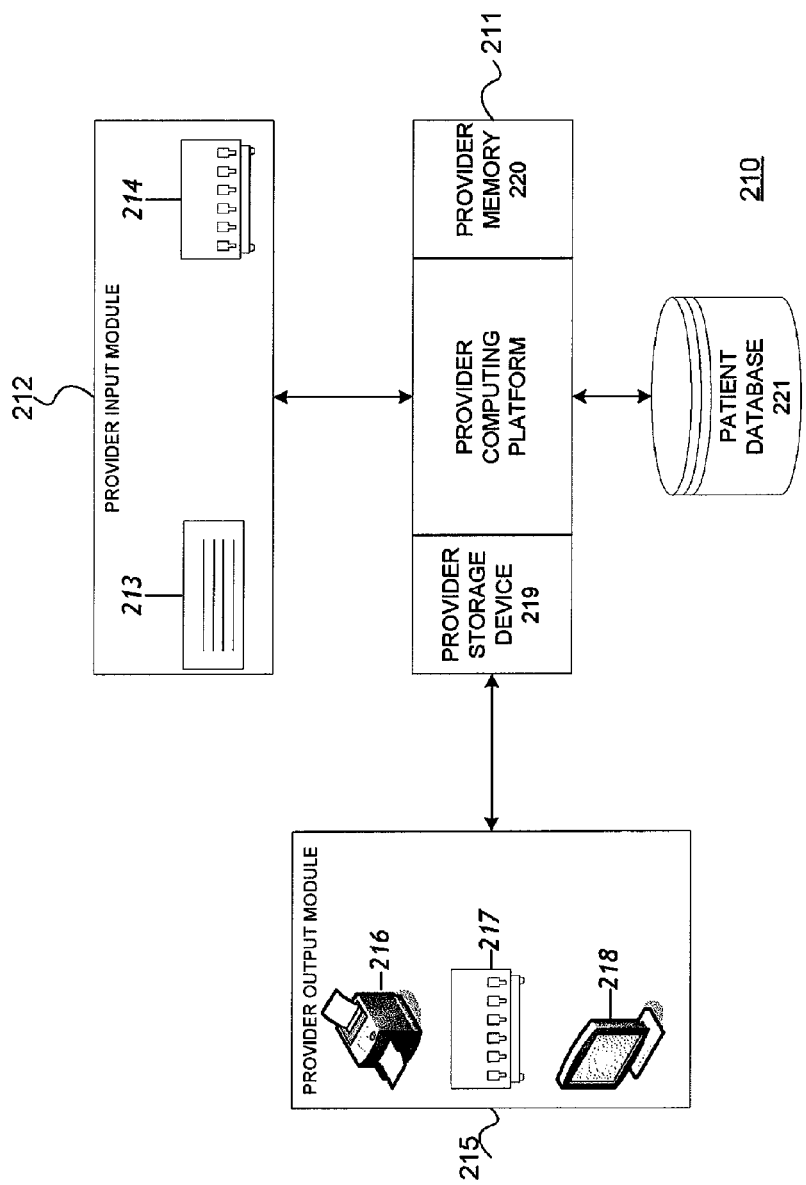
FIG. 3 illustrates the components of the healthcare provider system of FIG. 1, in accordance with one embodiment of the invention.

FIG. 3 illustrates a more detailed diagram of an exemplary healthcare provider system 210 of some embodiments of the present invention. In this example, healthcare provider system 210 facilitates the access to medical data.

As illustrated in FIG. 3, healthcare provider system 210 includes a provider computing platform 211, a provider input module 212, a provider output module 215, a provider memory 220, and a patient database 221. Provider computing platform 211 may be adapted to process input information received from provider input module 212. Provider computing platform 211 may further be adapted to provide output information to provider output module 215. Additionally, provider computing platform 211 may access information in patient database 221 for use in performing methods of the present invention.

Provider computing platform 211 may comprise a general purpose computer (e.g., a personal computer, network computer, server, or mainframe computer) having a processor or group of processors that may be programmed by executable code modules to perform one or more methods of the present invention. Provider computing platform 211 may also be implemented as set of two or more networked computing devices or nodes in a distributed network. Alternatively, provider computing platform 110 may be specially constructed (e.g., via application-specific circuitry) for carrying out methods of the present invention.

Provider input module 212 may include a provider input device 213 and/or a provider network interface 214. Provider input device 213 may be implemented using a keyboard, mouse, speech recognition device, and/or other data entry device. Provider network interface 214 may receive information over any type of network (not shown), such as a telephony-based network (e.g., PBX or POTS), a local area network, a wide area network, a dedicated intranet, and/or the Internet. Provider computing platform 212 may also access data stored on provider storage device 219. Provider storage device 219 may include a memory, such as RAM or ROM memory that contains instructions or data for performing one or more methods of the present invention.

In accessing medical data, provider input module 212 may be used to enter or obtain medical data from medical institutions, commands to be sent to medical institutions, requests to be sent to medical institutions, etc. Such information and requests may be obtained, for example, from an employee, from provider storage device 219, and/or from another computing system via provider network interface 214. Provider computing platform 211 may store such information received from provider input module 212 in patient database 221.

As further described below, provider computing platform 211 may use the stored patient information to generate reports, alerts, and the like for healthcare providers. Provider computing platform 211 may then output the requested information via provider output module 215.

Provider output module 215 may include a printer 216, a provider output interface 217, and/or a display 218. Printer 216 may be used to provide a printout to interested parties of relevant information, such medical data collected from etc. Provider output interface 217 may be used to provide such relevant information and/or other information to the interested parties via the Internet, email, fax, page, etc. or save the information on a computer readable medium. Display 218 may be used to provide such relevant information to interested parties visually.

Patient database 221 may include patient account data and healthcare provider data. Patient account data preferably includes a record of all personal data associated with patients connected to medical device 100, such as name, address, telephone number, driver's license number, social security number, credit card account number, checking account number, etc. Healthcare provider data preferably includes records of all reports generated for the healthcare providers, alerts generated for the healthcare providers, patients associated with the healthcare providers, requests made by the healthcare providers. Healthcare provider data may also include the healthcare provider's membership identification ("ID") and password. The information to be stored in patient database 221 may be entered or obtained using provider input module 212.

Figure 4:
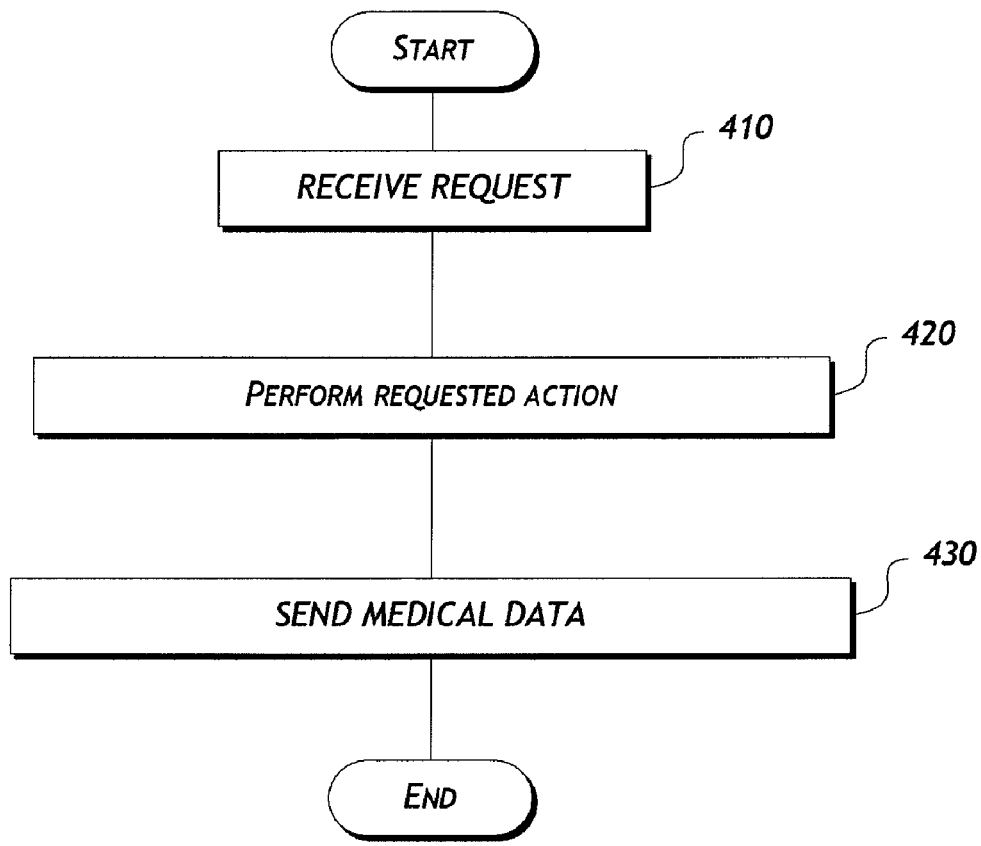
FIG. 4 illustrates a sequence of steps that may be performed by the medical device of FIG. 1, in accordance with one embodiment of the invention.

FIG. 4 illustrates a flowchart of an exemplary process for communicating medical data of some embodiments of the present invention. This process may be implemented by the medical device 100, and may be embodied in software and/or application-specific circuitry. Although the steps of the communication process are described as being performed in a particular order, one skilled in the art will appreciate that these steps may be performed in a modified or different order, or in an embodiment utilizing less than all of the steps described below. Further, one or more of the steps in FIG. 4 may be performed concurrently or in parallel.

First, embedded computing platform 110 receives a request (Step 410) generated by healthcare provider system 210. The request typically explicitly or implicitly specifies a particular action to be performed by medical device 100. In one embodiment, the request from the healthcare provider is sent to email server 220 which then sends the request to medical device 100. The request is received over network 230. In a preferred embodiment, the requests are received as emails using the POP protocol. That is, the healthcare provider sends the request to email server 220 using SMTP or IMAP protocols and then email server 220 forwards the email to the unique email address associated with medical device 100 using POP. Sending the requests as email messages may allow the communication and sending of data to medical device 100 even though the medical institution where medical device 100 exists has established a firewall. Embedded computing platform 110 may, in one embodiment, periodically check or request email server 220 to send medical device 100 any emails or requests that are to be sent to medical device 100. In another embodiment, email server 220 sends emails or requests directly to medical device 100 without waiting for a request. That is, in such an embodiment, medical device 100 does not periodically request or check for emails but receives the emails directly from email server 220 as they are received. Further, a skilled artisan will appreciate that a variety of other protocols could be used in embodiments of the present invention. For example, FTP, FTPS, SSH, HTTP, HTTPS, VOIP, GPS, CDMA, GSM, etc. may be used in some embodiments of the present invention. Moreover, a skilled artisan will appreciate that the email server 220 or another intermediate system can be configured with appropriate rules to prevent the medical device 100 from receiving unwanted messages or spam. For example, an incoming email addressed to the medical device 100 can be blocked if it is not from a trusted source, and/or if the message portion is not formatted properly (e.g., does not include a valid command or authentication signature).

Next, embedded computing platform 110 performs the requested action (Step 420). As part of this step, embedded computing platform 110 may parse the received request or email and perform the action as requested. A skilled artisan will appreciate that in some embodiments of the present invention, a protocol for communicating data between medical device 100 and healthcare provider system 210 via standard email messages may be established. As such, parsing of the request would be possible based on the defined protocol using conventional methods as is known in the art. If the received request relates to collecting medical data, embedded computing platform 110 may collect the requested medical data. If the received request relates to performing some other action (i.e., set parameters on a connected device, take an image, control some valve, etc.), embedded computing platform 110 can perform the requested action.

For example, in the preferred embodiment, various settings for the ventilator may need to be configured in order for them to be administered properly. Examples of commonly required settings to control a ventilator include: Peak Inspiratory Pressure (PIP) setting-limiting the peak pressure during inspiration of air; and Positive End Expiratory Pressure (PEEP) setting-limiting the peak pressure at the end of expiration of air. Many other ventilator settings may also be controlled. In addition, some ventilators are equipped with various sensors so that a patient caregiver may monitor the condition of the patient through the ventilator. Examples of commonly monitored parameters for a ventilator include Mean Airway Pressure (MAP)—the mean pressure measured within the airway during the breathing cycle; and Tidal Volume Inspired (Tvi)—measured volume of gas inhaled by the patient during a normal breath. Many other ventilator parameters may also be monitored. As a consequence, embedded computing platform 110 of the ventilator in the preferred embodiment may perform some action requested. Exemplary actions may include, "set PIP," "get ventilator data," "get MAP," "take image," etc. A skilled artisan will appreciate that a variety of other actions are possible in embodiments of the present invention.

In an alternate embodiment, embedded computing platform 110 automatically performs some action without waiting for a request (i.e., step 410 is skipped). In this embodiment, embedded computing platform 110 can be configured to perform some action automatically at predetermined intervals (e.g., daily, weekly, monthly, etc.). A skilled artisan will appreciate that the request received in step 410 may be a request to configure embedded computing platform 110 to perform some action automatically. For example, the request could configure embedded computing platform 110 to collect specified medical data every week. In this example, after receiving the request, embedded computing platform would collect the specified medical data every week automatically without waiting for a request.

In some embodiments, embedded computing platform 110 can be configured to perform some action automatically when a triggering event occurs. For example, embedded computing platform 110 may determine that medical device 100 has malfunctioned, that some readings from the patient are abnormal, that some patient readings have crossed some predetermined thresholds, etc. When such a triggering event occurs, embedded computing platform 110 may proactively send collected medical data by email to the healthcare provider system 210, without waiting for a request. The healthcare provider system 210 may set up such triggers by sending appropriate commands to the medical device 100 by email.

In Step 430 of FIG. 4, embedded computing platform 110 sends the collected medical data via an email message. As part of this step, embedded computing platform 110 sends the collected medical data to email server 220 via network 230 as an email message. The collected medical data may be formatted according to the defined protocol, as discussed above. A skilled artisan will appreciate that the collected medical data may constitute a confirmation or notification that embedded computing platform 110 has performed some action. Further, a skilled artisan will appreciate that the collected medical data may be empty (e.g., no notification or confirmation is desired). In one embodiment, embedded computing platform 110 may be adapted to send the data without performing analysis (i.e., send the raw collected data). In another embodiment, embedded computing platform 110 may be adapted to perform analysis prior to sending the collected medical data. For example, embedded computing platform 110 may generate reports, charts, trending or other quantitative analysis, web pages, applets to view the data, alerts, notifications, etc. that are sent in lieu of or along with the collected medical data. In yet another embodiment, embedded computing platform 110 may be adapted to generate medical images that are to be sent. For instance, embedded computing platform 110 may be configured to generate medical images using the Digital Imaging and Communications In Medicine (DICOM) format. DICOM was established in 1992 and is the standard for exchanging medical images in a digital format. These images can then be sent to email server 220. A skilled artisan will appreciate that medical images of any format may be generated in embodiments of the present invention. Further, in the preferred embodiment, embedded computing platform 110 emails the collected medical data, analysis, or images to email server 220 using the SMTP or IMAP protocols. A skilled artisan would appreciate that embedded computing platform 110 may send the medical data, analysis, or images to email server 220 also by using the protocols discussed above.

Figure 5:
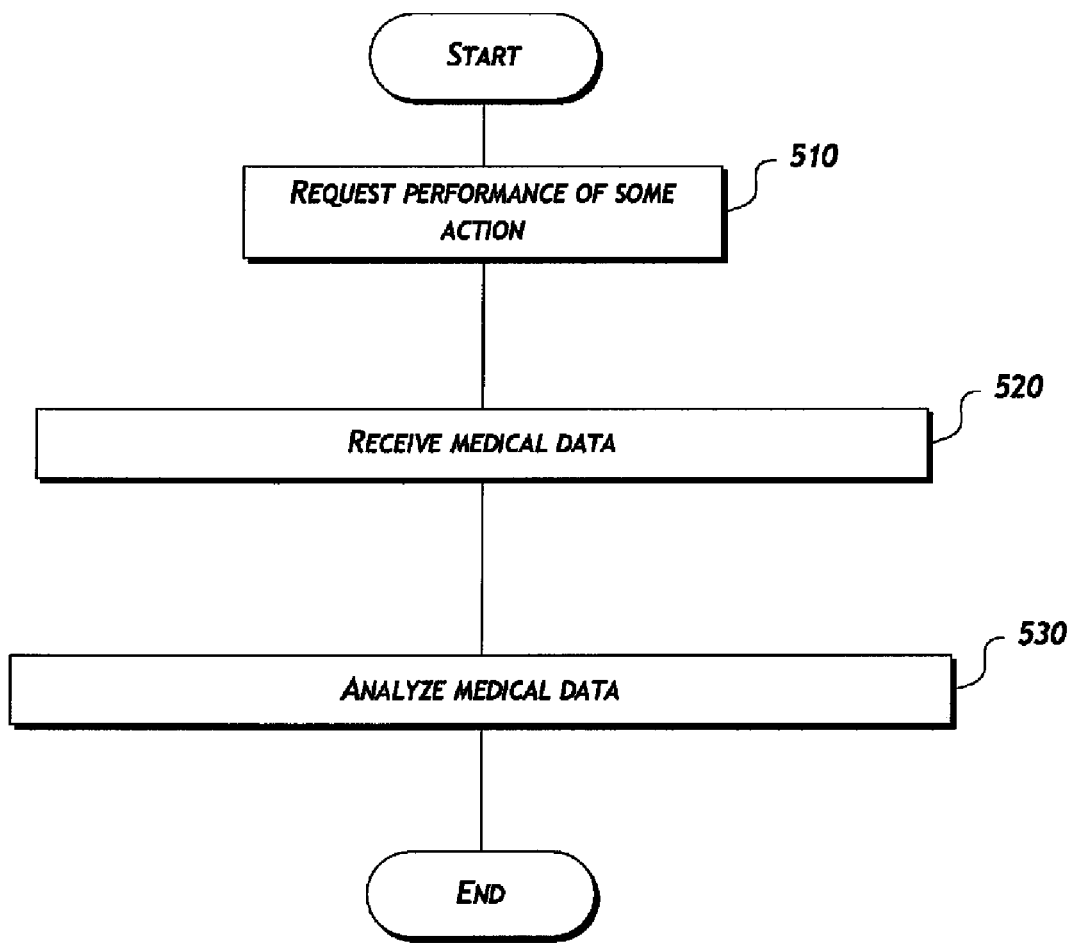
FIG. 5 illustrates a sequence of steps that may be performed by the healthcare provider system of FIG. 1, in accordance with one embodiment of the invention.

FIG. 5 illustrates a flowchart of an exemplary process by which a healthcare provider system 210, and particularly the provider computing platform 211 (FIG. 3) of such a system, requests and receives medical data in some embodiments of the present invention. Although the steps of the communication process are described as being performed in a particular order, one skilled in the art will appreciate that these steps may be performed in a modified or different order, or in an embodiment utilizing less than all of the steps described below. Further, one or more of the steps in FIG. 5 may be performed concurrently or in parallel.

First, as discussed above, provider computing platform 211 requests performance of some action (Step 510). In a preferred embodiment, the healthcare provider submits the request using a web page, and the request is transmitted to email server 220 over the Internet. The web page may be a dedicated web page for a healthcare provider program. Special log-ins may also be provided such that only members can submit requests. A skilled artisan will appreciate that the healthcare provider can input information regarding the request using any known input mechanism provided by one or more web pages or other user interface, such as pull-down menus, text boxes, selection boxes, hyperlinks, mobile applications, and the like. Further, a skilled artisan will appreciate that the request may also be inputted by use of a dedicated software program, application, device, etc. For example, the requests may be inputted by use of an applet, plug-in, extension, add-on, etc. A skilled artisan would appreciate that, for example, that medical device 100 could provide an applet that could be used to generate requests and provider computing platform 211 may download the applet and use the applet to create the requests. One of ordinary skilled in the art would appreciate that the web page accessed by provider computing platform 211 could invoke the applet to be downloaded. Similarly, a plug-in, extension, or add-on could be installed on computing platform 211 and be used to generate requests.

Moreover, the request may be formatted according to the defined protocol, as discussed above. For example, once a human operator specifies the target medical device and the type of data to be collected, application software may transform these selections into an appropriately formatted and addressed email message that can be interpreted by the medical device 100. In one embodiment, the application software is a web-based application hosted on a web application server (see FIG. 10B).

The request from the healthcare provider is then sent to email server 220 over network 230. In the preferred embodiment, the requests are sent as emails using the SMTP or IMAP protocols. In an alternate embodiment, provider computing platform 211 automatically sends a request for performance of some action without waiting for a request from the healthcare provider. In this embodiment, provider computing platform 211 can be configured to send requests to medical device 100 at predetermined intervals (e.g., daily, weekly, monthly, etc.). Moreover, if the healthcare provider is not already registered, the healthcare provider may also register with the system at this point, and may be given a membership ID and/or password. Information supplied by the healthcare provider during and after registration is maintained in patient database 221. Further, a skilled artisan will appreciate that a variety of other protocols could be used in embodiments of the present invention. For example, FTP, FTPS, SSH, HTTP, HTTPS, VOIP, GPS, CDMA, GSM, etc. may be used.

Next, provider computing platform 211 receives the requested medical data (Step 520) from email server 220, which receives the collected medical data from medical device 100. In the preferred embodiment, provider computing platform 211 receives the medical data as an email message from email server 220 using the POP protocol. Provider computing platform 211 may, in one embodiment, periodically check or request email server 220 to send any emails or medical data that are to be sent to provider computing platform 211. In another embodiment, email server 220 sends emails or medical data directly to provider computing platform 211 without waiting for a request. That is, in such an embodiment, provider computing platform 211 does not periodically request or check for emails or medical data but receives the emails or medical data directly from email server 220 as they are received. Moreover, in an alternative embodiment, email server 220 does not send all the data to provider computing platform 211. Email server 220 stores the received medical data and sends a notification to provider computing platform 211 that medical data has been received. The provider computing platform 211 may then provide direct access to the medical data stored at email server 220 or may temporarily download a copy of the medical data as desired. A skilled artisan would appreciate that many modifications of the above are possible in embodiments of the present invention. For instance, provider computing platform 211 after temporarily downloading a copy of the medical data can request that email server 220 delete its copy of the medical data or the deletion can occur automatically.

In addition, in one embodiment, healthcare provider system 210 comprises an application server and a client device. In this embodiment, provider computing platform 211 is part of the application server and the application server can be located inside or outside the medical institution. As such, email server 220 sends any medical data to application server. Then application server analyzes the medical data (see step 530 below) and sends client device a notification (discussed below). Alternatively, application server can just store and analyze the received medical data without sending a notification to the client device such that the client device can access the data at any time desired. In another embodiment, healthcare provider system 210 comprises only a client device. In this embodiment, there is no application server and email server 220 sends any medical data to the client device directly. As such, the client device analyses the medical data (see step 530 below). Further, a skilled artisan would appreciate that provider computing platform 211 may receive the medical data from email server 220 also by using the various protocols discussed above.

The received medical data is then analyzed (Step 530). As part of this step, a healthcare provider reviews the received medical data. A skilled artisan will appreciate that the received medical data may also be parsed based on the defined protocol, as discussed above. In the embodiment including the application server, the application server receives the medical data from email server 220 and analyzes the data. The application server may create reports, charts, alerts, web pages, etc. for viewing by the healthcare provider. The reports, alerts, charts, web pages, etc. may relate to the status of medical device 100, status of patients connected to medical device 100, malfunctions associated with medical device 100, etc. The application server also may also create a webpage which would enable the viewing of, and alteration to the functions and performance parameters of medical device 100. After the application server has analyzed the medical data, a notification can be sent to a client device associated with a healthcare provider. The notification notifies the healthcare provider that medical data has been received and analyzed. The notification can be sent to device, such as a mobile phone, pager, personal digital assistant, computer, or the like, associated with a healthcare provider. In the embodiment where the analysis is performed by medical device 100, the application server can send the notification without performing the analysis. Subsequently, the healthcare provider can access the medical data. For instance, the healthcare provider may access a secure web page provided by the application server to view any reports, charts, alerts, etc. that were generated in response to the received medical data. Alternatively, the application server can store the received medical data and the analysis without sending a notification to the client device. In that case, the client device can access the data and analysis as discussed above when desired.

In the embodiment where there is no application server, the client device performs the analysis discussed above. In this embodiment, the client device alerts the healthcare provider directly that medical data has been received and analyzed. In the embodiment where the analysis is performed by medical device 100, the client can alert the healthcare provider without performing the analysis. The healthcare provider then can access the analyzed medical data via the client device. Alternatively, the client device may send a notification to a device, such as a mobile phone, pager, personal digital assistant associated with the healthcare provider and then the healthcare can access the analyzed medical data via the client device.

A skilled artisan would appreciate that, similar to the disclosure above for generating requests, the received medical data can also be viewed by the use of a dedicated software program, application, device, applet, plug-in, extension, add-on, etc. A skilled artisan would appreciate that a variety of graphs, reports, charts, etc. can be used to view the received medical data. For instance, a line graph or chart can be used to view medical data monitored from a ventilator. As another example, a display using an applet may be used to display trending data received from a ventilator. The applet could be generated by medical device 100, application server, or the client device as discussed above.

Figure 6:
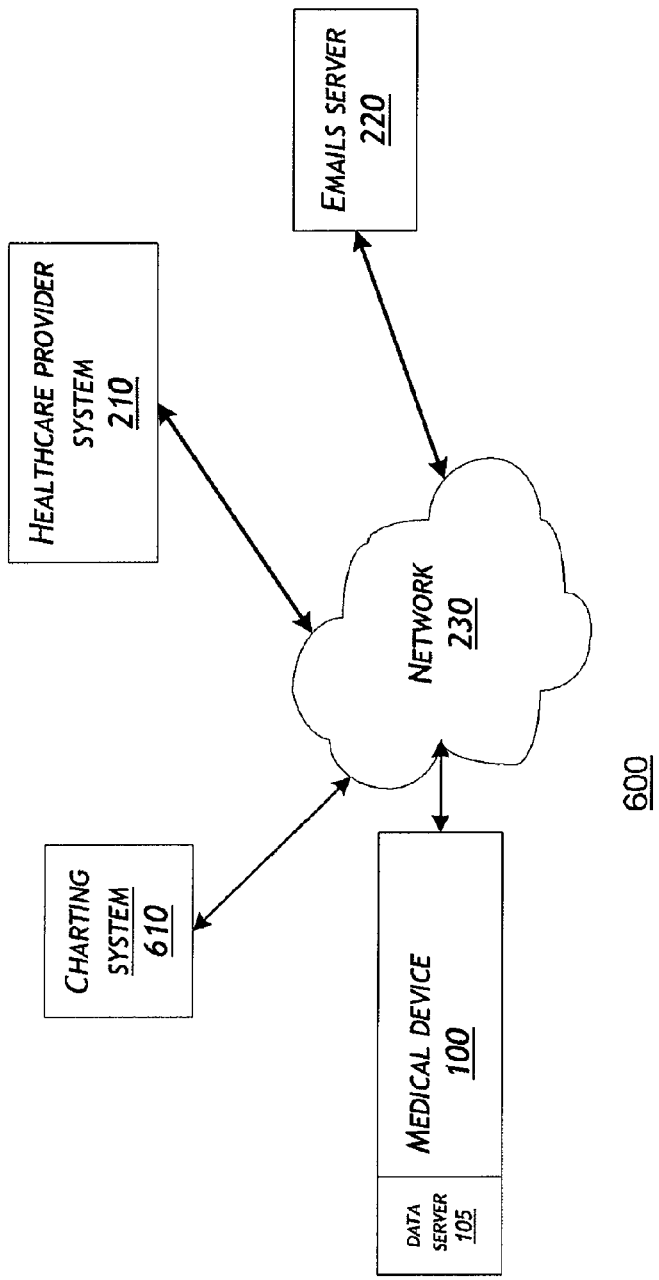
FIG. 6 is a block diagram of the system according to another embodiment.

FIG. 6 illustrates an exemplary system environment 600 for providing medical charting in some embodiments of the present invention. Similar to system 200 above in FIG. 1, system 600 may comprise multiple computer systems, such as a, a healthcare provider system 210, a medical device 100 containing a data sever 105, and an email server 220. In addition, system 600 contains a charting system 610. These various components may be connected and communicate with one another through any suitable network 230, including the Internet.

Charting system 610 is maintained by a medical institution. Charting system 610 is used by a medical institution to chart medical data collected from patients. One example of a charting system is Clinivision MPC Software that allows for the download of data from the Puritan Bennett® Ventilators directly to the charting device computer. The ventilator data is automatically integrated into the patient chart report, and users can create ventilator flow sheet reports.

However, one problem with current charting systems, is that medical device 100 must be configured to output data in a specified format so that the medical data can properly be processed by the charting system. For example, the Puritan Bennett ventilators, discussed above, must be configured to output medical data in a specified format that can be processed by the Clinivision charting software. As such, if the charting software is modified or a different charting software product is used, medical device 100 would have to be re-configured to output medical data in a different format. This can be done by replacing medical device 100 with a different medical device or manually updating the functioning of medical device 100 by uploading a different version of the software that enables outputting the medical data in a different format. This can be troublesome if multiple medical devices have been installed because multiple medical devices may have to be replaced or updated manually.

In one embodiment, medical device 100 may be re-configured to output medical data in a different format electronically. Similar to the discussions above, medical device 100 is configured to communicate with email server 220. Email server 220 is configured to communicate with healthcare provider system 210 which is configured to communicate with charting system 610. As such, medical device 100 can be configured to output medical data in a standard format to email server 220. Then when the medical data is communicated to healthcare provider system 210, healthcare provider system 210 can be adapted to format the received medical data in a specified format and transfer the formatted medical data to charting system 610 such that charting system 610 can process the medical data. This embodiment enables the installation of a different charting program without re-configuring medical device 100. Medical device 100 can still communicate medical data in a standard format and healthcare provider system 210 can be reconfigured to format the medical data in a different format as may be needed by the different charting program.

To enable proper reformatting of the received medical data, healthcare provider system 210 can be adapted to map the received medical data in a standard format to medical data in a specified format for charting system 610. That is, healthcare provider system 210 may have a mapping table that associates medical data in the standard format to the related variables, fields, or function calls of charting system 610. A skilled artisan will appreciate that this embodiment will work if healthcare provider system 210 includes an application server or does not include an application server, as discussed above. If healthcare provider system 210 includes an application server, then application server can be configured to re-format the medical data as needed. If healthcare provider system 210 does not include an application server, then the client device can be configured to re-format the data and transfer the data to charting system 610. A skilled artisan will also appreciate that the standard format can be any format desired, even a format that can be directly processed by a particular charting system.

In another embodiment, medical device 100 can be updated to output medical data in a specified format. For example, the ventilators, as discussed above, that output medical data in a specified format for processing by the Clinivision charting software can be updated. In this embodiment, as discussed above, medical device 100 can be configured to receive a request from email server 220. In this embodiment, the request may include a software update for medical device 100. This software update would configure medical device 100 to output the medical data in a different format. A skilled artisan will appreciate that similar software updates can also be sent to healthcare provider system 210 in some embodiments of the present invention. For example, if healthcare provider system 210 includes an application server and a new charting program is now being used, a software update can be sent to the application server to provide mapping of medical data to the format needed for the new charting program. Similar updating can also be provided if healthcare provider system 210 does not include an application server and includes only a client device.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors. The code modules may be stored in any type of computer-readable medium or other computer storage device. Some or all of the methods may alternatively be embodied in specialized computer hardware. In addition, the components referred to herein may be implemented in hardware, software, firmware, or a combination thereof.

The disclosed features may be implemented in various environments, including computer-based environments, such as personal computers, workstations, servers, laptops, personal digital assistants (PDAs), mobile phones, handheld devices, and other computing devices, workstation, networked and other computing-based environments with one or more customers. The present invention, however, is not limited to such examples and embodiments of the invention may be implemented with other platforms and in other environments.

By way of example, some embodiments of the invention may be implemented using conventional personal computers (PCs), desktops, hand-held devices, multiprocessor computers, pen computers, microprocessor-based or programmable customer electronics devices, minicomputers, mainframe computers, personal mobile computing devices, mobile phones, portable or stationary personal computers, palmtop computers or the like. As used herein, the term "computing system" is intended to encompass a single computer or computing device, and is also intended to encompass a collection of computers or computing devices that interact with each other (e.g., over a network). The term "server" is intended to encompass any computing system that responds (or is programmed or configured to respond) to requests by sending or "serving" information. The term "node" is intended to encompass a computing system that is addressable on a network.

The storage media referred to herein symbolize elements that temporarily or permanently store data and instructions. Although storage functions may be provided as part of a computer, memory functions can also be implemented in a network, processors (e.g., cache, register), or elsewhere. Various types of storage mediums can be used to implement features of the invention, such as a read-only memory (ROM), a random access memory (RAM), or a memory with other access options. Further, memory functions may be physically implemented by computer-readable media, such as, for example: (a) magnetic media, like a hard disk, a floppy disk, a magnetic disk, a tape, or a cassette tape; (b) optical media, like an optical disk (e.g., a CD-ROM), or a digital versatile disk (DVD); (c) semiconductor media, like DRAM, SRAM, EPROM, EEPROM, memory stick, and/or by any other media, like paper.

Some embodiments of the invention may also include computer program products that are stored in a computer-readable medium or transmitted using a carrier, such as an electronic carrier signal communicated across a network between computers or other devices. In addition to transmitting carrier signals, network environments may be provided to link or connect components in the disclosed systems. Networking environments are commonplace in offices, enterprise-wide computer networks, intranets and the Internet (i.e., the World Wide Web). The network may be a wired or a wireless network. To name a few network implementations, the network may be, for example, a local area network (LAN), a wide area network (WAN), a public switched telephone network (PSTN), an Integrated Services Digital Network (ISDN), an infrared (IR) link, a radio link, such as a Universal Mobile Telecommunications System (UMTS), Global System for Mobile Communication (GSM), Code Division Multiple Access (CDMA), or a satellite link.

Transmission protocols and data formats are also known, such as, for example transmission control protocol/internet protocol (TCP/IP), hyper text transfer protocol (HTTP), secure HTTP, wireless application protocol, unique resource locator (URL), unique resource identifier (URI), hyper text markup language (HTML), extensible markup language (XML), extensible hyper text markup language (XHTML), wireless application markup language (WML), Standard Generalized Markup Language (SGML), etc. Such features may be utilized to implement some embodiments of the present invention, as disclosed herein.

Figure 7:
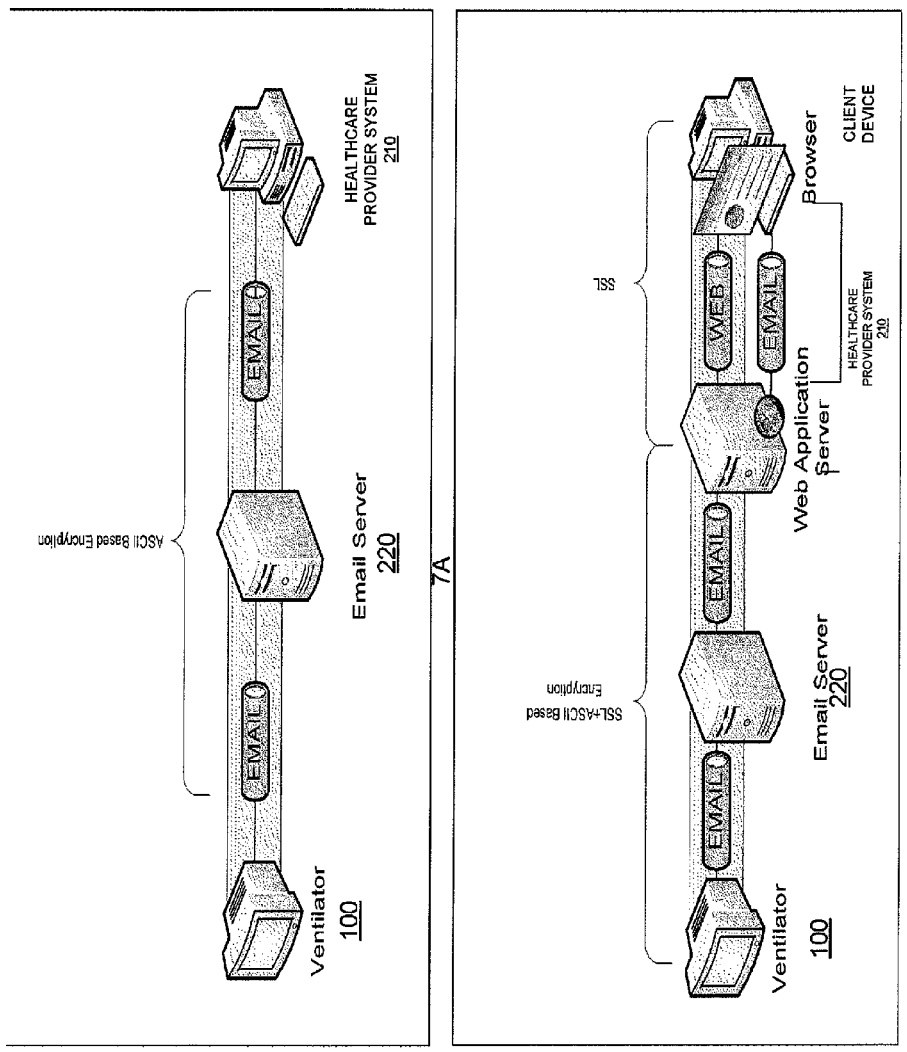
FIG. 7 illustrates one example of architecture for encryption, in accordance with one embodiment of the invention.

Moreover, to comply with HIPAA, data may be communicated in embodiments of the present invention using known encryption and decryption techniques. For example, FIG. 7 shows an exemplary encryption system for the preferred embodiment of the present invention. As shown in FIG. 7 (7A and 7B), communication from medical device 100 (e.g., ventilator) to email server 220 and communications from email server 220 and healthcare provider system 210 may be encrypted using the secure socket level (SSL) protocol. This type of encryption can be used in both embodiments relating to healthcare provider system 210. That is SSL can be used if healthcare provider system 210 includes only a client device, as shown in FIG. 7A, or if healthcare provider system 210 includes an application server and a client device, as shown if FIG. 7B. In the embodiment with the application server, as shown in FIG. 7B, SSL may also be used in communications between the application server and the client device.

Further, as also shown in FIG. 10, on top of the SSL level, all communication from and to medical device 100 are preferably protected using ASCII based security measures. In one embodiment, three layers of ASCII based security based measures may be used. The first layer may relate to cryptographic hash functions, such as MD5. The second level may relate to data blocking and stuffing. The third level may relate to private-key stream ciphering. Modifications and variations of these layers are possible in embodiments of the present invention. Additionally, a skilled artisan will appreciate that a variety of other encryption algorithms may be used in embodiments of the present invention.

In the particular embodiment shown in FIG. 10B, the application software which runs on the web application server is responsible for at least the following tasks: (1) transforming user selections made via an Internet-connected web browser and a web page into an appropriately formatted request message, such as an email, to send to the designated medical device 100; (2) sending this request message via the email server 220 to the medical device 100; (3) receiving the corresponding reply message, such as an email, generated by the medical device 100, and parsing this reply message to extract the requested data; (4) storing the extracted data in a database in association with the request message and the healthcare entity that generated the request, and (5) making this data, and other collected data, available via web-based interface.

It should be emphasized that many variations and modifications may be made to the above-described embodiments, the elements of which are to be understood as being among other acceptable examples. All such modifications and variations are intended to be included herein within the scope of this disclosure. Further, nothing in the foregoing disclosure is intended to imply that any particular component, characteristic or process step is essential.

What is claimed:

1. A computer-implemented method of communicating with a client system over a network, the method comprising:
   receiving, by a network device and from the client system over the network using a first protocol, an email message comprising a command;
   formatting the received email message so that the command can be communicated to a medical apparatus using a second protocol;
   transmitting the command to the medical apparatus, wherein the network device is physically connected to the medical apparatus;
   receiving a response from the physically connected medical apparatus after the physically connected medical apparatus has processed the command;
   generating a response email message comprising the received response;
   generating a report related to the received response; and
   transmitting the response email message and the report to the client system over the network;
   wherein elements or functions may be executed out of order from that shown or discussed including substantially concurrently or in reverse order, depending on the functionality involved; and
   wherein three layers of ASCII based security based measures may be used: the first layer may relate to cryptographic hash functions, such as MD5; the second level may relate to data blocking and stuffing; the third level may relate to private-key stream ciphering.

2. The method of claim 1, wherein the physically connected medical apparatus is a ventilator.

3. The method of claim 1, wherein the network device is located within a medical institution.

4. The method of claim 3, wherein the medical institution includes a firewall.

5. The method of claim 1, further comprising storing the received response in a data storage located within the network device.

6. A computer-implemented method of communicating with a client system over a network, the method comprising:
   receiving, by a network device, medical data from a medical apparatus, wherein the medical apparatus is physically connected to the network device;
   generating an applet for displaying the received medical data;
   generating an email message comprising the received medical data; and
   sending the email message and the applet to the client system over the network;
   wherein elements or functions may be executed out of order from that shown or discussed, including substantially concurrently or in reverse order, depending on the functionality involved; and
   wherein three layers of ASCII based security based measures may be used: the first layer may relate to cryptographic hash functions, such as MD5; the second level may relate to data blocking and stuffing; the third level may relate to private-key stream ciphering.

7. The method of claim 6, wherein the network device further generates reports related to the medical data and performs trending analysis on the medical data.

8. The method of claim 6, wherein the medical apparatus is a ventilator.

9. The method of claim 6, wherein the network device further stores the medical data.

10. A device for connecting a medical apparatus to a network, the device comprising:
    a first port for physically connecting the device to the medical apparatus;
    a second port for connecting the device to the network;
    a data storage system for storing medical data received from the physically connected medical apparatus; and
    a computer system configured to:
    receive an email message including a request for medical data associated with the physically connected medical apparatus;
    transmit the request to the physically connected medical apparatus;

receive medical data from the physically connected medical apparatus using a first protocol;
store the received medical data for future analysis;
format the received medical data for transmission using a second protocol; and
generate an applet for displaying the received medical data;
wherein elements or functions may be executed out of order from that shown or discussed, including substantially concurrent or in reverse order, depending on the functionality involved; and wherein three layers of ASCII based security based measures may be used: the first layer may relate to cryptographic hash functions, such as MD5; the second level may relate to data blocking and stuffing; the third level may relate to private-key stream ciphering.

11. The device of claim 10, wherein the physically connected medical apparatus is a ventilator.

* * * * *